United States Patent
Zhou et al.

(10) Patent No.: US 8,401,614 B2
(45) Date of Patent: Mar. 19, 2013

(54) MAGNETIC RESONANCE THERMOMETRY METHOD

(75) Inventors: Xiao Dong Zhou, Shenzhen (CN); Cheng Ni, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 503 days.

(21) Appl. No.: 12/708,838

(22) Filed: Feb. 19, 2010

(65) Prior Publication Data
US 2010/0217114 A1    Aug. 26, 2010

(30) Foreign Application Priority Data
Feb. 20, 2009    (CN) .......................... 2009 1 0004957

(51) Int. Cl.
*A61B 5/05*    (2006.01)
(52) U.S. Cl. ......... 600/412; 600/407; 600/410; 600/411
(58) Field of Classification Search ................. 600/407, 600/410, 411, 412, 415; 324/300, 307, 315
See application file for complete search history.

(56) References Cited

U.S. PATENT DOCUMENTS

| | | | | |
|---|---|---|---|---|
| 5,291,890 | A | * | 3/1994 | Cline et al. ..................... 600/411 |
| 6,559,644 | B2 | * | 5/2003 | Froundlich et al. ........... 324/315 |
| 2004/0027127 | A1 | * | 2/2004 | Mills .............................. 324/317 |

OTHER PUBLICATIONS

"Monitoring and correcting spatio-temporal variations of the MR scanner's static magnetic field" by A.M. El-Sharkawy et al. Magn Reson Mater Phy 19: 223-236, 2006.*

* cited by examiner

*Primary Examiner* — Jacqueline Cheng
*Assistant Examiner* — Jason Ip
(74) *Attorney, Agent, or Firm* — Schiff Hardin LLP

(57) ABSTRACT

A method for reducing errors in the measurement of temperature by magnetic resonance, for use in magnetic resonance imaging-guided HIFU equipment, includes acquiring an MR phase image, as a reference image, before heating an area to be heated with the HIFU equipment; acquiring another MR phase image, as a heated image, during or after the heating by the HIFU equipment; and calculating the temperature change in the heated area according to said heated image and said reference image; and making compensation to said temperature change according to the change in the magnetic field caused by the position change of an ultrasonic transducer in said HIFU equipment. The method can reduce significantly the temperature errors resulting from the position changes of the ultrasonic transducer.

7 Claims, 2 Drawing Sheets

MAGNETIC RESONANCE THERMOMETRY METHOD

BACKGROUND OF THE INVENTION

1. Field of the Invention

The present invention relates to the field of high intensity focused ultrasound (HIFU) monitored by magnetic resonance imaging (MRI) and, particularly, to a method for reducing errors in the measurement of temperature of MRI guided HIFU equipment.

2. Description of the Prior Art

Magnetic resonance (MR) thermometry based on proton resonance frequency (PRF) shift can be used to monitor temperature changes in an area heated by HIFU in MRI-guided HIFU equipment, based on the phenomenon of the resonance frequency of the protons in water being offset (shifted) dependent on the temperature change. MR thermometry based on PRF-shift requires that a base image (MR phase image) before heating, also referred to as a reference image, be generated, with the reference image providing information on a reference phase. By subtraction from the phase image (also referred to as a heated image) acquired during heating or after heating, the exact value of the elevated temperature in the heated area can be determined.

During a practical heating process, however, after the reference image is acquired changes may occur in the position of the ultrasonic transducer (i.e. the treatment head), and the susceptibility change resulting from the movements of the ultrasonic transducer causes changes in the static magnetic field of the focal region of the ultrasonic transducer, so that the subtraction of the heated image and the reference image produces an additional phase difference, thus causing errors in the temperature measurement.

Currently, there are mainly two common solutions for reducing temperature errors. One of the solutions can be referred to as a single reference image method wherein after the reference image has been acquired, the movement range of the ultrasonic transducer is restricted, so as to restrict the temperature errors within an acceptable range. However, since the spatial range used by a reference image is very small, while the ultrasonic transducer moves within a relatively large spatial range in the HIFU treatment process, it is necessary to acquire reference images frequently for various positions in order to measure the temperature of each focal position of the ultrasonic transducer, and this increases the complexity of the temperature measurement and the overall treatment time.

The other solution for reducing temperature errors can be referred to as a self-reference method, i.e. not acquiring any reference images, but instead utilizing the heated images themselves to obtain the reference phase by a polynomial fitting and extrapolation of the phase from the non-heated region. The temperature change monitored using this method is limited to the vicinity of the focus of HIFU, and it is very difficult in practical applications to monitor the temperature changes outside the focus point. Furthermore, the accuracy of the polynomial fitting and extrapolation and the complexity of the phase image are dependent on the size of the heated area, and it is relatively difficult to obtain stable, consistent and accurate results in general.

SUMMARY OF THE INVENTION

An object of the present invention is to provide a method for reducing errors in the measurement of temperature by a magnetic resonance imaging method, for use in obtaining accurate temperature change in a heated area.

The present invention provides a method for reducing errors in the measurement of temperature by a magnetic resonance imaging method, for use in MRI guided HIFU equipment, that includes acquiring an MR phase image, as a reference image, before heating an area to be heated with the HIFU equipment; acquiring another MR phase image, as a heated image, during or after the heating by the HIFU equipment, and calculating the temperature change in the heated area according to the heated image and the reference image, and automatically compensating the temperature change according to a change in the magnetic field caused by a position change of an ultrasonic transducer in said HIFU equipment.

Preferably, the compensation of the temperature change is made according to the following equation, $$\Delta T = \Delta T_{conv} - \frac{y \cdot [\Delta B_{t(r2)} - \Delta B_{t(r1)}] \cdot T_E}{y \cdot B_0 \cdot \alpha \cdot T_E}$$

wherein, $\Delta T$ represents the value of the temperature change after being compensated; $\Delta T_{conv}$ represents the value of the temperature change calculated according to the heated image and said reference image; $[\Delta B_{t(r2)} - \Delta B_{t(r1)}]$ represents the change in the magnetic field caused by the position change of the ultrasonic transducer from a position r1 to position r2; $\gamma$ represents the gyromagnetic ratio of hydrogen atomic nuclei; $B_0$ represents the static magnetic field strength; and $\alpha$ represents a temperature-frequency coefficient.

In a preferred embodiment, the method further includes measuring the magnetic field produced by the ultrasonic transducer in water as the change in the magnetic field caused by the position change of the ultrasonic transducer.

The ultrasonic transducer has a support (mount). During the measuring of the magnetic field caused by the ultrasonic transducer, the support is put into and taken out of water together with the ultrasonic transducer.

Preferably, the equation $$\Delta B_t = (\phi_1 - \phi_2)/(\gamma \cdot T_E)$$

is used to calculate the magnetic field $\Delta B_t$ caused by the ultrasonic transducer, wherein $\phi_1$ represents a first phase image acquired when the ultrasonic transducer is in water; $\phi_2$ represents a second phase image acquired when the ultrasonic transducer is not in water; $\gamma$ represents the gyromagnetic ratio of hydrogen atomic nuclei; and $T_E$ represents an echo time.

In another preferred embodiment, the method further includes calculating the magnetic field caused by the ultrasonic transducer as the change of the magnetic field caused by the position change of the ultrasonic transducer.

The steps of calculating the magnetic field caused by the ultrasonic transducer include dividing the ultrasonic transducer into a number of finite volume elements, calculating the magnetic dipole moment of each finite volume element, and calculating the magnetic field in space produced by the magnetic dipole moment of each finite volume element, and summing the magnetic field produced by each finite volume element to obtain the magnetic field caused by said ultrasonic transducer.

From the abovementioned solutions it can be seen that since the present invention compensates the temperature measurement according to the magnetic field caused by the ultrasonic transducer, it can reduce significantly the temperature errors resulting from the position changes of the ultrasonic transducer. In comparison with the existing single reference image method, the present invention does not need to acquire a large number of reference images for different positions of the ultrasonic transducer, so the complexity of the temperature measurement is reduced and the speed of the whole treatment process is increased. In comparison with the existing self-reference method, the present invention can accurately obtain the temperature changes in the heated area, thus providing stable results of temperature measurement.

DESCRIPTION OF THE PREFERRED EMBODIMENTS

Figure 1:
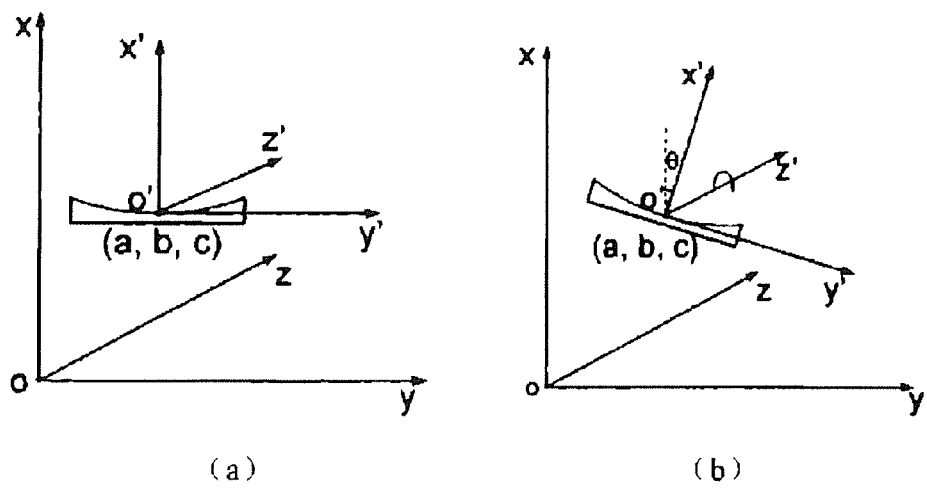
FIG. 1 schematically illustrates the coordinate system of the ultrasonic transducer and the coordinate system of the magnet in an embodiment of the present invention.

FIG. 1 is a schematic diagram of a coordinate system of the ultrasonic transducer and a coordinate system of the magnet in an embodiment of the present invention, in which the coordinate system xyz represents the coordinate system of the magnetic body, and the coordinate system x' y' z' represents the coordinate system of the ultrasonic transducer, wherein (a) represents that the ultrasonic transducer is located at the original position, and (b) represents the position of the ultrasonic transducer after having been rotated about the direction of the magnetic field $B_0$.

Figure 2:
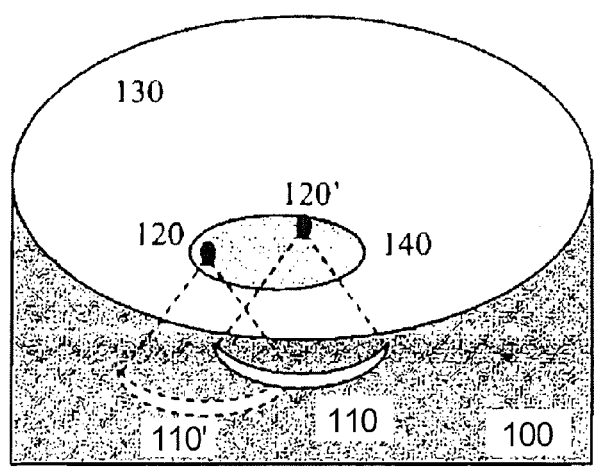
FIG. 2 schematically illustrates the movement of the ultrasonic transducer in an embodiment of the present invention.

FIG. 2 is a schematic diagram of the movement of the position of the ultrasonic transducer in the embodiment of the present invention, in which 100 represents a water tank, 110 and 110' respectively represent the ultrasonic transducer before and after being moved, 120 and 120' respectively represent the focus points corresponding to 110 and 110', 130 represents the body of a patient, and 140 represents the area heated by HIFU equipment, such as a tumor.

Figure 3:
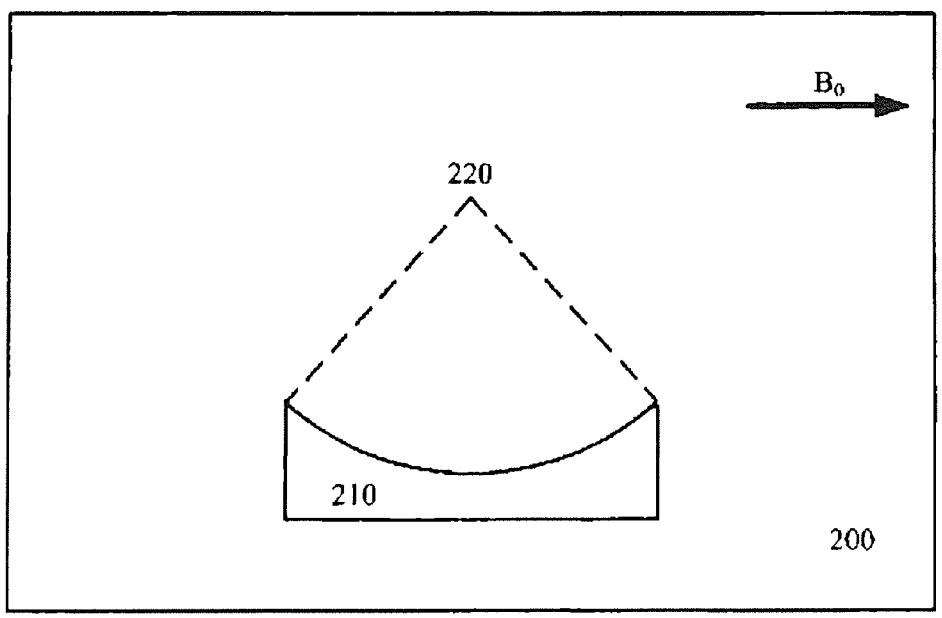
FIG. 3 schematically illustrates a device for measuring the magnetic field caused by the ultrasonic transducer, in accordance with the present invention.

FIG. 3 is a schematic diagram showing the device for measuring the magnetic field caused by an ultrasonic transducer, in which, 200 represents a water tank, 210 represents the ultrasonic transducer, and 220 represents the focus point of the ultrasonic transducer, and the support of the ultrasonic transducer is not shown.

In order to explain the objects, technical solutions and advantages of the present invention, the present invention will be described in detail below in the context of a particular embodiment.

Gradient echo sequences are used to measure an MR phase image, and since the local temperature in the measured tissue is changing, the proton resonance frequency changes with it, while the change of the proton resonance frequency can be reflected in the MR phase image. Accordingly, the temperature change can be expressed as:

$$\Delta T = \frac{\Delta \varphi}{\gamma \cdot B_0 \cdot \alpha \cdot T_E} \quad (1)$$

in which, $\Delta T$ represents the temperature change, $\gamma$ represents the gyromagnetic ratio of the hydrogen atomic nuclei (for a proton, it represents $42.58 \times 10^6$ Hz/T), $B_0$ represents the static magnetic field intensity, $T_E$ represents the echo time, $\alpha$ represents the temperature frequency coefficient, and $\Delta \phi$ represents the phase difference before and after the ultrasonic transducer of the HIFU equipment releasing ultrasonic energy (heating), that is:

$$\Delta \phi = \phi_T - \phi_R \quad (2)$$

and in equation (2), the phase image $\phi_R$ is acquired before the heating by the HIFU equipment, and the phase image $\phi_T$ is acquired when it is being heated by the HIFU equipment or after it has been heated by the HIFU equipment.

The ideal magnetic field for the MRI equipment is a uniform field, however, since an inherent non-uniform field distribution $\Delta B_c$ exists in the actual magnetic field B, the actual magnetic field B is:

$$B(x,y,z) = B_0 + \Delta B_c(x,y,z) \quad (3)$$

In the MRI guided HIFU equipment, the ultrasonic transducer will also introduce an additional magnetic field $\Delta B_t$ into the existing magnetic field. Since there is no nonlinear magnetic substance (ferromaterial, etc.) in the MRI imaging area, in the case of the ultrasonic transducer transversely moving or rotating about the $B_0$ direction, the spatial distribution of $\Delta B_t$ is constant with respect to the ultrasonic transducer. If $\Delta B_t (x, y, z)$ is used to represent the induced magnetic field when the ultrasonic transducer is in the position $r=(a, b, c)$, and $\Delta B_t (x', y', z')$ is used to represent the induced magnetic field in the case of the ultrasonic transducer only transversely moving without rotating, $\Delta B_{t(r)}(x, y, z)$ is a translation of $\Delta B_t (x', y', z')$, which can be calculated by the following equation:

$$\Delta B_{t(r)}(x,y,z) = \Delta B_t(x-a, y-b, z-c) \quad (4)$$

As shown in FIG. 1, taking into consideration that the ultrasonic transducer is rotated at an angle $\theta$ along $B_0$, then $\Delta B_{t(r)} (x, y, z)$ can be calculated by the following equation:

$$\Delta B_{t(r)}(x,y,z) = \Delta B_t(x',y',z') \quad (5)$$

wherein
  $x' = x \cos \theta + y \sin \theta - a$
  wherein $y' = -x \sin \theta + y \cos \theta - b$
  $z' = z - c$.

As shown in FIG. 2, when the ultrasonic transducer is located at the position 1 (i.e. the position where the ultrasonic transducer 110 is located), $r1=(x_1, y_1, z_1)$, and this time, the magnetic field can be expressed as:

$$B_R(x,y,z) = B_0 + \Delta B_c(x,y,z) + \Delta B_{t(r1)}(x,y,z) \quad (6).$$

An MR phase image is acquired at the position 1 as a reference image, and this time, the measured phase image can be expressed as:

$$\phi_R = g \cdot B_{R1} \cdot T_E \quad (7).$$

When the ultrasonic transducer is moved to the position 2 (i.e. the position where the ultrasonic transducer 110' is located), $r2=(x_2, y_2, z_2)$, and this time, the magnetic field can be expressed as:

$$B_{r2}(x,y,z) = B_0 + \Delta_c(x,y,z) + \Delta B_{t(r2)}(x,y,z) \quad (8).$$

An MR phase image is acquired at the position 2, and this time, the acquired phase image can be expressed as:

$$\phi_T = \gamma \cdot (B_{r2} \cdot \alpha \cdot \Delta T_E) \quad (9).$$

wherein, $\Delta T$ is a value of temperature change in the heated area.

According to the equations (6) to (9):

$$\Delta T = \frac{(\varphi_T - \varphi_R)}{\gamma \cdot B_{r_2} \cdot \alpha \cdot T_E} - \frac{\gamma \cdot [\Delta B_{t(r2)} - \Delta B_{t(r1)}] \cdot T_E}{\gamma \cdot B_{r2} \cdot \alpha \cdot T_E} \quad (10)$$

In the equation (10), the first term is a value $\Delta T_{conv}$ of temperature change obtained by calculating the difference of the phase images, which is equivalent to a value of temperature change obtained by the conventional PRF thermometry. A second term is a temperature error caused by the magnetic field change $\Delta B_{pos}(=\Delta B_{t(r2)} - \Delta B_{t(r1)}$ resulting from the position change of the ultrasonic transducer.

In practical use, since $\Delta B_c$ is at the level of only several millionths of the magnitude of the $B_0$, and the influence of $\Delta B_t$ on $B_0$ can be ignored, $B_{r2}$ in the equation (10) may be replaced by $B_0$. Therefore, the equation (10) can be converted into:

$$\Delta T = \Delta T_{conv} - \frac{\gamma \cdot [\Delta B_{t(r2)} - \Delta B_{t(r1)}] \cdot T_E}{\gamma \cdot B_0 \alpha \cdot T_E} \quad (11).$$

The magnetic field change $\Delta B_t$ caused by the position change of the ultrasonic transducer can be obtained by numerical calculations or by experimental measurements, which will be described below, respectively.

In a static magnetic field, when the ultrasonic transducer is placed in a water tank, due to the difference in the susceptibility between the ultrasonic transducer and the water, the local magnetic field will change. Accordingly, the magnetic field resulting from the ultrasonic transducer in the water can be obtained through measurements in tests, which can be used as the magnetic field change $\Delta B_t$ resulting from the position change of the ultrasonic transducer. In FIG. 3, an MR phase image is acquired respectively when the ultrasonic transducer exists in the water and when the ultrasonic transducer does not exist in the water, thus measuring the change $\Delta B_t$ in the magnetic field.

A flowchart of measuring the magnetic field caused by the ultrasonic transducer will be described below with reference to FIG. 3, and the flowchart mainly comprises the following steps:

Step 01, place a water tank 200 in the magnetic resonance equipment, with the water tank 200 being preferably made of a non-magnetic material, such as plastic, etc.

Step 02, place the ultrasonic transducer 210 in the water tank, and make the position and direction of the ultrasonic transducer 210 identical to the position and direction in the practical heating.

Step 03, charge water into the water tank 200.

Step 04, use the magnetic resonance imaging equipment, and use gradient echo sequences to acquire a first phase image $\phi_1$. For example, the parameters of the sequences can be set as $T_R/T_E$=20 ms/15 ms.

Record the liquid level in the water tank 200 in step 03 or step 04.

Step 05, take the ultrasonic transducer 210 out of the water tank, and charge water into the water tank 200 to restore the liquid level at the time when the ultrasonic transducer 200 was placed therein. During this period of time, the position of the water tank 200 is kept unchanged.

Step 06, use the magnetic resonance imaging equipment to acquire a second phase image $\phi_2$, wherein the gradient echo sequences use the same parameters as those in acquiring the first phase image $\phi_1$.

Step 07, obtain the magnetic field $\Delta B_t$ resulting from the, ultrasonic transducer 210 by calculating according to the first phase image $\phi_1$ and the second phase image $\phi_2$, for example, the following equation can be used:

$$\Delta B_t = (\phi_1 - \phi_2)/(\gamma \cdot T_E)$$

During the above process, the support of the ultrasonic transducer 210 can be put into and taken out of the water tank together with the ultrasonic transducer. This can also compensate at the same time for the temperature errors caused by the support.

If the geometric structure of the ultrasonic transducer and the susceptibility of the material can be obtained, then the magnetic field resulting from the ultrasonic transducer can be obtained by calculating with the numerical calculation method, which can be used as the magnetic field change caused by the position change of the ultrasonic transducer. The method of obtaining $\Delta B_t$ by numerical calculation will be described below. The method mainly includes the following steps:

Step 11, divide the ultrasonic transducer into a plurality of finite volume elements.

Step 12, calculate the magnetic dipole moment of each finite volume element.

Step 13, calculate the magnetic field produced by the magnetic dipole moment in each finite volume element at every point in space. For example, the magnetic field produced by the magnetic dipole moment of each finite volume element at every point in space can be calculated by using the Biot-Savart-Laplace Law.

Step 14, the magnetic field caused by the ultrasonic transducer at every point in space equals the sum of the magnetic fields produced by each finite volume element at the point, so by summing the magnetic field produced by each finite volume element the magnetic field $\Delta B_t$ caused by the ultrasonic transducer can be obtained.

After the magnetic field caused by the ultrasonic transducer has been obtained, the above equation (10) is used to compensate the temperature change in the heated area, thus obtaining the accurate temperature change.

In summary, the method in the embodiment of the present invention proceeds as follows: acquiring an MR phase image as a reference image before the HIFU equipment having heated the area to be heated; acquiring another MR phase image, as a heated image, when the HIFU equipment is heating or after it has heated. The temperature change of the heated area is calculated according to the heated image and the reference image. The temperature change is compensated according to the magnetic field caused by the ultrasonic transducer.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for reducing errors in a measurement of temperature by magnetic resonance in a high intensity focused ultrasound (HIFU) procedure using magnetic resonance imaging-guide HIFU equipment, comprising:

before heating, with said HIFU equipment, an area of a subject located within a magnetic resonance imaging apparatus, operating said magnetic resonance imaging apparatus to acquire a magnetic resonance phase image, as a reference image, of a region of the subject comprising said area, the operation of said magnetic resonance imaging apparatus including generating a static magnetic field therein, and said HIFU equipment comprising an ultrasonic transducer comprised of a material that causes a change in said static magnetic field when a position of said ultrasonic transducer changes within said magnetic resonance imaging apparatus;

operating said magnetic resonance imaging apparatus to acquire another magnetic resonance phase image of said region of said patient, as a heated image, during or after heating of said area by said HIFU equipment;

supplying said reference image and said heated image to a processor and, in said processor, automatically calculating a temperature change in the heated area from said heated image and said reference image; and in said processor, automatically making compensation to said temperature change by identifying and using said change in said static magnetic caused by a position change of said ultrasonic transducer in said magnetic resonance apparatus.

2. The method as claimed in claim 1, comprising making the compensation to said temperature change according to the equation, $$\Delta T = \Delta T_{conv} - \frac{[\Delta B_{t(r2)} - \Delta B_{t(r1)}]\cdot}{B_0 \cdot \alpha \cdot}$$

wherein, $\Delta T$ represents a value of the temperature change after being compensated; $\Delta T_{conv}$ represents the value of the temperature change calculated according to said heated image and said reference image; $[\Delta B_t(r2) - \Delta B_{t(r1)}]$ represents the change in the magnetic field caused by the position change of said ultrasonic transducer from a position r1 to position r2; $B_0$ represents an intensity of the static magnetic field intensity; and $\alpha$ represents a temperature frequency coefficient.

3. The method as claimed in claim 1, comprising measuring a magnetic field produced by said ultrasonic transducer in water, and using said change in the static magnetic field caused by the position change of said ultrasonic transducer.

4. The method as claimed in claim 3, wherein said ultrasonic transducer has a support, and comprising, during the measuring of the magnetic field caused by said ultrasonic transducer, putting said support into and taking said support out of water together with said ultrasonic transducer.

5. The method as claimed in claim 3, comprising using the equation $$\Delta B_t = (\phi_1 - \phi_2)/(\gamma \cdot T_E)$$

to calculate the magnetic field $\Delta B_t$ caused by said ultrasonic transducer, wherein $\phi_1$ represents a first phase image acquired when the ultrasonic transducer is in water; $\phi_2$ represents a second phase image acquired when the ultrasonic transducer is not in water; $\gamma$ represents the gyromagnetic ratio of hydrogen atomic nuclei; and $T_E$ represents an echo time.

6. The method as claimed in claim 1, comprising calculating a magnetic field caused by said ultrasonic transducer as the change of the static magnetic field caused by the position change of said ultrasonic transducer.

7. The method as claimed in claim 6, comprising calculating the magnetic field caused by said ultrasonic transducer by:

dividing said ultrasonic transducer into a plurality of finite transducer volume elements;

calculating a magnetic dipole moment of each finite transducer volume element, and calculating a magnetic field in space produced by the magnetic dipole moment of each finite transducer volume element; and summing the magnetic field in space produced by each finite volume element to obtain the magnetic field caused by said ultrasonic transducer.

* * * * *